United States Patent
Denk et al.

(10) Patent No.: US 10,537,305 B2
(45) Date of Patent: Jan. 21, 2020

(54) DETECTING AMNIOTIC FLUID POSITION BASED ON SHEAR WAVE PROPAGATION

(71) Applicant: General Electric Company, Schenectady, NY (US)

(72) Inventors: Stefan Denk, Oberösterreich (AT); Martin Paul Mienkina, Oberöesterreich (AT)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1069 days.

(21) Appl. No.: 14/870,426

(22) Filed: Sep. 30, 2015

(65) Prior Publication Data

US 2017/0086783 A1    Mar. 30, 2017

(51) Int. Cl.
*A61B 8/08* (2006.01)
*A61B 8/00* (2006.01)

(52) U.S. Cl.
CPC .......... *A61B 8/0866* (2013.01); *A61B 8/5207* (2013.01); *A61B 8/5269* (2013.01); *A61B 8/54* (2013.01)

(58) Field of Classification Search
CPC ... A61B 8/0866; A61B 8/5207; A61B 8/5269; A61B 8/54
See application file for complete search history.

(56) References Cited

U.S. PATENT DOCUMENTS

| | | | |
|---|---|---|---|
| 6,614,360 B1 | 9/2003 | Leggett, III et al. | |
| 7,039,524 B2 | 5/2006 | Haugland | |
| 2013/0066204 A1 | 3/2013 | Fan et al. | |
| 2013/0218011 A1* | 8/2013 | Benson | A61B 8/485 600/438 |
| 2015/0080730 A1* | 3/2015 | Kanayama | A61B 8/5207 600/447 |
| 2016/0310107 A1* | 10/2016 | Mansi | A61B 8/463 |

* cited by examiner

*Primary Examiner* — Peter Luong
(74) *Attorney, Agent, or Firm* — McAndrews, Held & Malloy, Ltd.; Jacob Groethe; David Bates

(57) ABSTRACT

Various embodiments include systems and methods for detecting amniotic fluid position based on shear wave propagation. Ultrasound image data may be acquired, and shear wave related data for an area corresponding to the acquired ultrasound image data may also be acquired. Identification data associated with one or more particular structures or elements within the area may be generated based on the shear wave related data, and ultrasound imaging during an ultrasound examination may then be controlled based on the identification data. The ultrasound imaging may comprise generating and rendering one or more ultrasound images based on the acquired ultrasound image. The ultrasound examination may be obstetric (OB) ultrasound examination, with the area comprising one or more of: at least portion of a fetus, amniotic fluid surrounding the fetus, and tissue of a mother carrying the fetus.

20 Claims, 4 Drawing Sheets

DETECTING AMNIOTIC FLUID POSITION BASED ON SHEAR WAVE PROPAGATION

CLAIMS OF PRIORITY

[Not Applicable]

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to methods and systems for detecting amniotic fluid position based on shear wave propagation.

BACKGROUND OF THE INVENTION

Ultrasound imaging is a medical imaging technique for imaging organs and soft tissues in a human body. Ultrasound imaging uses real time, non-invasive high frequency sound waves to produce ultrasound images. These ultrasound images may be two-dimensional (2D), three-dimensional (3D), and/or four-dimensional (4D) images.

Different objects and/or different structures associated therewith may be subject to the ultrasound imaging, and/or may need to be illustrated accurately and/or be distinguishable from one another in ultrasound images. For example, during obstetric (OB) ultrasound imaging, the objects subject to the ultrasound imaging may typically include the fetus and the mother. Thus, OB ultrasound images (or data corresponding thereto) would include structures associated with the fetus, as well as surrounding structures associated with the mother (e.g., mother's tissues, organs, etc.). There may also be additional objects and/or structures which may be pertinent in OB ultrasound imaging, such as the amniotic fluid contained by the amniotic sac of the mother, in which the fetus is suspended. The various objects and/or structures may not be very clearly distinguishable from one another, or certain objects and/or structures may not be sufficiently captured in ultrasound images.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for detecting amniotic fluid position based on shear wave propagation, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Figure 1:
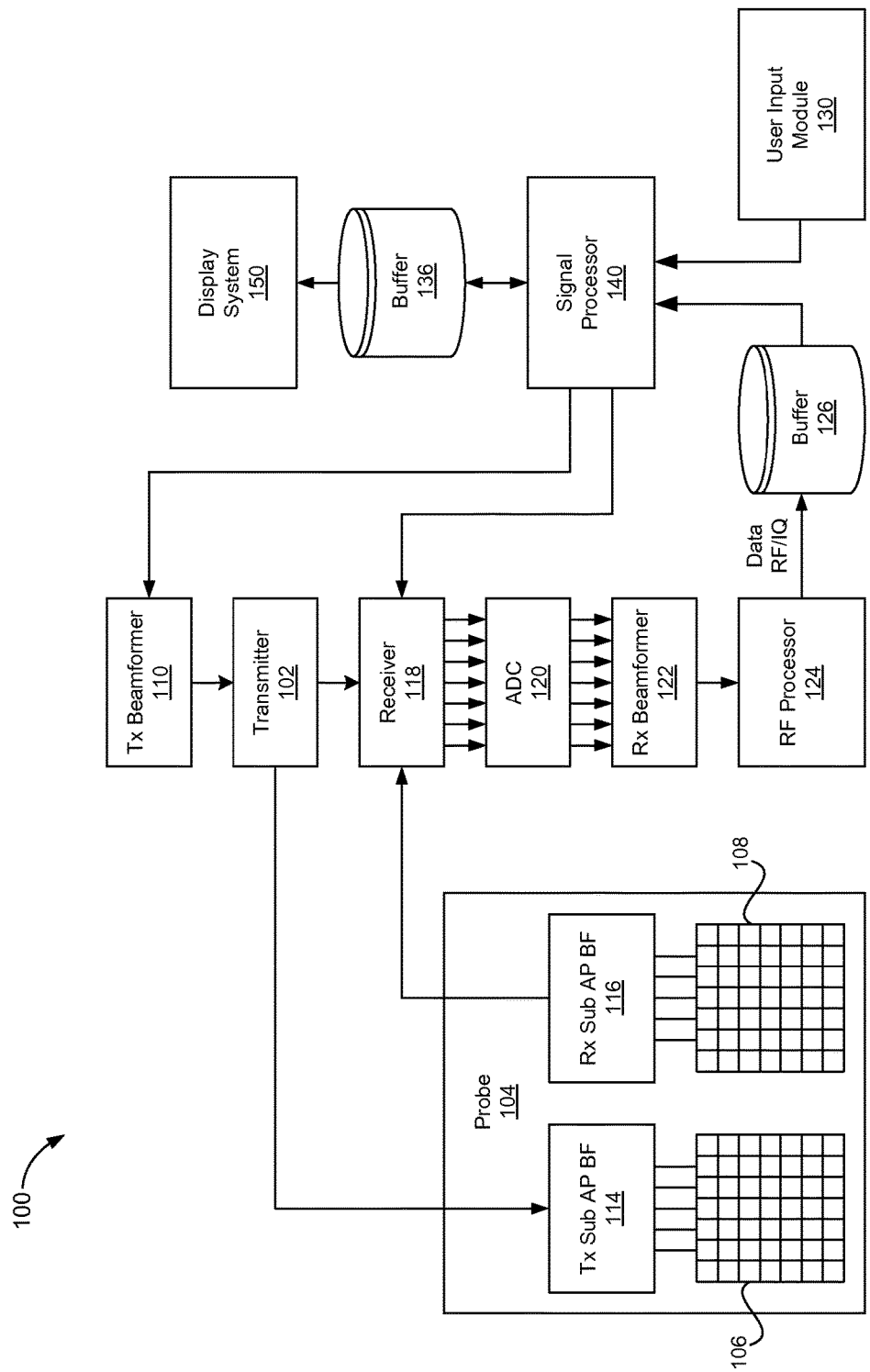
FIG. 1 is a block diagram illustrating an example ultrasound system that may be used in ultrasound imaging, which may support amniotic fluid position detection based on shear wave propagation, in accordance with various embodiments of the invention.

Certain embodiments of the invention may be found in methods and systems for optimizing detection of amniotic fluid based on shear wave propagation, and/or for use of that detection in enhancing rendering of ultrasound images. For example, aspects of the present invention have the technical effect of detection of amniotic fluid based on shear wave propagation, and/or for use of that detection in enhancing rendering of ultrasound images by acquiring ultrasound image data, acquiring shear wave related data for an area corresponding to the acquired ultrasound image data, and generating based on the shear wave related data, identification data associated with one or more particular structures or elements within the area. Ultrasound imaging during an ultrasound examination may then be controlled based on the identification data. The ultrasound imaging may comprise generating and rendering one or more ultrasound images based on the acquired ultrasound image. In this regard, controlling the ultrasound imaging may comprise controlling the generating and/or the rendering of the one or more ultrasound images based on the identification data. Controlling the ultrasound imaging may comprise optimizing rendering of one or more other structures or elements in the area based on the identification data.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "an embodiment," "one embodiment," "a representative embodiment," "an example embodiment," "various embodiments," "certain embodiments," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

In addition, as used herein, the phrase "pixel" also includes embodiments of the present invention where the data is represented by a "voxel." Thus, both the terms "pixel" and "voxel" may be used interchangeably throughout this document.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC, or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams." Also, forming of images may be performed using channel combinations that may originate from more than one transmit event (e.g., synthetic aperture techniques).

In various embodiments, ultrasound processing, including visualization enhancement, to form images may be performed, for example, in software, firmware, hardware, or a combination thereof. One implementation of an ultrasound system in accordance with various embodiments is illustrated in FIG. 1.

FIG. 1 is a block diagram illustrating an example ultrasound system that may be used in ultrasound imaging, which may support amniotic fluid position detection based on shear wave propagation, in accordance with various embodiments of the invention. Shown in FIG. 1 is an ultrasound system 100.

The ultrasound system 100 comprises, for example, a transmitter 102, an ultrasound probe 104, a transmit beamformer 110, a receiver 118, a receive beamformer 122, a RF processor 124, a RF/IQ buffer 126, a user input module 130, a signal processor 140, an image buffer 136, and a display system 150.

The transmitter 102 may comprise suitable circuitry that may be operable to drive an ultrasound probe 104. The transmitter 102 and the ultrasound probe 104 may be implemented and/or configured for one dimensional (1D), two-dimensional (2D), three-dimensional (3D), and/or four-dimensional (4D) ultrasound scanning. In this regard, ultrasound probe 104 may comprise a one dimensional (1D, 1.25D, 1.5D or 1.75D) array or a two dimensional (2D) array of piezoelectric elements. For example, as shown in FIG. 1, the ultrasound probe 104 may comprise a group of transmit transducer elements 106 and a group of receive transducer elements 108, that normally constitute the same elements. The transmitter 102 may be driven by the transmit beamformer 110.

The transmit beamformer 110 may comprise suitable circuitry that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). In this regard, the group of transmit transducer elements 106 can be activated to transmit ultrasonic signals. The ultrasonic signals may comprise, for example, pulse sequences that are fired repeatedly at a pulse repetition frequency (PRF), which may typically be in the kilohertz range. The pulse sequences may be focused at the same transmit focal position with the same transmit characteristics. A series of transmit firings focused at the same transmit focal position may be referred to as a "packet."

The transmitted ultrasonic signals may be back-scattered from structures in the object of interest, like tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116 and are then communicated to the receiver 118.

The receiver 118 may comprise suitable circuitry that may be operable to receive and demodulate the signals from the probe transducer elements or receive sub-aperture beamformer 116. The demodulated analog signals may be communicated to one or more of the plurality of A/D converters (ADCs) 120.

Each plurality of A/D converters 120 may comprise suitable circuitry that may be operable to convert analog signals to corresponding digital signals. In this regard, the plurality of A/D converters 120 may be configured to convert demodulated analog signals from the receiver 118 to corresponding digital signals. The plurality of A/D converters 120 are disposed between the receiver 118 and the receive beamformer 122. Notwithstanding, the invention is not limited in this regard. Accordingly, in some embodiments of the invention, the plurality of A/D converters 120 may be integrated within the receiver 118.

The receive beamformer 122 may comprise suitable circuitry that may be operable to perform digital beamforming processing to, for example, sum the delayed channel signals received from the plurality of A/D converters 120 and output a beam summed signal. The resulting processed information may be converted back to corresponding RF signals. The corresponding output RF signals that are output from the receive beamformer 122 may be communicated to the RF processor 124. In accordance with some embodiments of the invention, the receiver 118, the plurality of A/D converters 120, and the beamformer 122 may be integrated into a single beamformer, which may be digital.

The RF processor 124 may comprise suitable circuitry that may be operable to demodulate the RF signals. In some instances, the RF processor 124 may comprise a complex demodulator (not shown) that is operable to demodulate the RF signals to form In-phase and quadrature (IQ) data pairs (e.g., B-mode data pairs) which may be representative of the corresponding echo signals. The RF (or IQ) signal data may then be communicated to an RF/IQ buffer 126.

The RF/IQ buffer 126 may comprise suitable circuitry that may be operable to provide temporary storage of output of the RF processor 124—e.g., the RF (or IQ) signal data, which is generated by the RF processor 124.

The user input module 130 may comprise suitable circuitry that may be operable to enable obtaining or providing input to the ultrasound system 100, for use in operations thereof. For example, the user input module 130 may be used to input patient data, surgical instrument data, scan parameters, settings, configuration parameters, change scan mode, and the like. In an example embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 122, the RF processor 124, the RF/IQ buffer 126, the user input module 130, the signal processor 140, the image buffer 136, and/or the display system 150.

The signal processor 140 may comprise suitable circuitry that may be operable to process the ultrasound scan data (e.g., the RF and/or IQ signal data) and/or to generate corresponding ultrasound images, such as for presentation on the display system 150. The signal processor 140 is operable to perform one or more processing operations according to a plurality of selectable ultrasound modalities on the acquired ultrasound scan data. In some instances, the signal processor 140 may be operable to perform compounding, motion tracking, and/or speckle tracking. Acquired ultrasound scan data may be processed in real-time—e.g., during a B-mode scanning session, as the B-mode echo signals are received. Additionally or alternatively, the ultrasound scan data may be stored temporarily in the RF/IQ buffer 126 during a scanning session and processed in less than real-time in a live or off-line operation.

In operation, the ultrasound system 100 may be used in generating ultrasonic images, including two-dimensional (2D), three-dimensional (3D), and/or four-dimensional (4D) images. In this regard, the ultrasound system 100 may be operable to continuously acquire ultrasound scan data at a particular frame rate, which may be suitable for the imaging situation in question. For example, frame rates may range from 20-70 but may be lower or higher. The acquired ultrasound scan data may be displayed on the display system 150 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several seconds' worth of frames of ultrasound scan data. The frames of ultrasound scan data are stored in a manner to facilitate retrieval thereof according to its order or time of acquisition. The image buffer 136 may be embodied as any known data storage medium.

In some instances, the ultrasound system 100 may be configured to support grayscale and color based operations. For example, the signal processor 140 may be operable to perform grayscale B-mode processing and/or color processing. The grayscale B-mode processing may comprise processing B-mode RF signal data or IQ data pairs. For example, the grayscale B-mode processing may enable forming an envelope of the beam-summed receive signal by computing the quantity $(I^2+Q^2)^{1/2}$. The envelope can undergo additional B-mode processing, such as logarithmic compression to form the display data. The display data may be converted to X-Y format for video display. The scan-converted frames can be mapped to grayscale for display.

The B-mode frames that are provided to the image buffer 136 and/or the display system 150. The color processing may comprise processing color based RF signal data or IQ data pairs to form frames to overlay on B-mode frames that are provided to the image buffer 136 and/or the display system 150. The grayscale and/or color processing may be adaptively adjusted based on user input—e.g., a selection from the user input module 130, for example, for enhance of grayscale and/or color of particular area.

In some instances, different objects and/or structures may be subject to the ultrasound imaging, and/or may need to be shown distinctively (from one another) in rendered ultrasound images. The various objects and/or structures may not very clearly distinguishable from one another and/or certain objects and/or structures may not be sufficiently captured in ultrasound images. This may be particularly relevant in such applications as obstetric (OB) ultrasound examinations. In this regard, during OB ultrasound imaging, ultrasound images (or data corresponding thereto) may include or correspond to the fetus (or structures associated therewith), structures associated with mother surrounding or adjacent to the fetus (e.g., tissue, nearby organs, etc.), and also certain additional objects and/or structures, such as the amniotic fluid in which the fetus is suspended. Failure (or difficulty) in discriminating between the different objects or structures may adversely affect OB ultrasound examinations. In this regard, quality and/or results (e.g., visualization, measurements, etc.) of OB ultrasound examination may depend on objects and/or structures being clearly distinguishable from each other—e.g., the fetus and/or structures associated therewith particularly being clearly distinguishable from other objects and/or structures in the areas subject to ultrasound imaging.

Thus, successfully and accurately identifying and locating the amniotic fluid—that is the clear discrimination between fetus and amniotic fluid—may allow for enhanced separation of the fetus from other objects and/or structures, particularly the mother's tissue, which in turn may result in optimized performance—e.g., enhanced visualization and/or rendering of details of the fetus (e.g., facial features, etc.), enhanced measurements, etc. This may not be always possible, however, which may result in degraded performance. For example, in many instances the amniotic fluid may not be located fully during OB ultrasound imaging, due to such causes as reverberations, clutter, etc. Thus, as a result when trying to do facial imaging of the fetus (producing easy to understand views of the fetus, typically its face), for example, it may be challenging to distinguish between the mother's tissue and the fetus. Overcoming such challenges may require a lot of experience and/or scan time from the operator, and even with that it may still be challenging to produce views of the fetus with acceptable quality.

Accordingly, in various embodiments adaptive measures may be taken to identify particular objects and/or structures in areas corresponding to the ultrasound images (or acquired data corresponding thereto), generate identification data corresponding to the particular objects and/or structures (and/or other objects and/or structures), and/or to use such identification data in enhancing and/or optimizing ultrasound imaging (including, e.g., quality of rendering of corresponding ultrasound images, and information that may be derived therefrom).

For example, shear waves may be used to help identify particular objects and/or structures (e.g., fluids, such as amniotic fluid in OB use scenarios) which may exhibit particular characteristics in response to shear wave propagation. In this regard, because ultrasonic shear waves cannot propagate in fluids, they may be used in detecting fluids (including the amniotic fluid in OB ultrasound examinations). Thus, shear waves may be applied during OB ultrasound imaging, with the results or data obtained from these shear waves being used to better identify and locate the amniotic fluid. In other words, use of the shear waves may be used in improving the segmentation of the amniotic fluid and the fetus, respectively, thus facilitating better results—e.g., better measurement and visualization results. For example, once the amniotic fluid between the probe and fetus is detected and accurately located using the shear wave propagation, rendering of the fetus (and/or surrounding mother's tissue) may be optimized, such as by placing the render-start inside the amniotic fluid which could simplify the 3D/4D rendering process significantly.

With reference to the ultrasound system 100 illustrated in FIG. 1, for example, the ultrasound probe 104 may be operable to emit shear waves, and to capture echo signals of the emitted shear wave propagation. The captured echo signals may then be handled substantially in the same manner and/or via the same path described above. The captured shear wave echo signals may then be processed, such as via the signal processor 140 for example. In this regard, the processing of the shear wave echo signals may be configured to provide data that would allow identifying particular objects and/or structures, such as the amniotic fluid during OB ultrasound imaging. For example, the signal processor 140 may determine based on the captured shear wave echo signals, the signal-to-noise ratio (SNR) for the applied shear wave propagation. The SNR may then be used in determining or estimating location of fluids (e.g., the amniotic fluid) which may be associated with low SNR. In this regard, determining when SNR is sufficiently low may be based on particular thresholds, which may be pre-set or pre-programmed, and/or may be adjusted or re-set thereafter. Thus, regions meeting the pre-set shear wave propagation criteria (e.g., low SNR) may be segmented as being particular object—e.g., amniotic fluid. This segmentation can be employed as an additional weighting for B-mode brightness, e.g. high probability of amniotic fluid leads to high B-mode brightness reduction.

The signal processor 140 may also be operable to apply the identification data obtained based on assessment of the shear wave propagation to enhance overall quality and/or performance. For example, the segmentation of the amniotic fluid as described above may be utilized in enhancing the rendering of the ultrasound images via the display 150. This may be done by using the segmentation of the amniotic fluid in controlling the rendering process. For example, the render start may be placed based at the amniotic fluid area and/or the amniotic fluid area may be masked from rendering (to increase the success in 3D/4D rendering), the location of the amniotic fluid area (or information relating thereto) may be used as an additional weighting for B-mode brightness control—e.g., with regions corresponding to high probability of amniotic fluid by subject to high B-mode brightness reduction, etc.

Figure 2A:
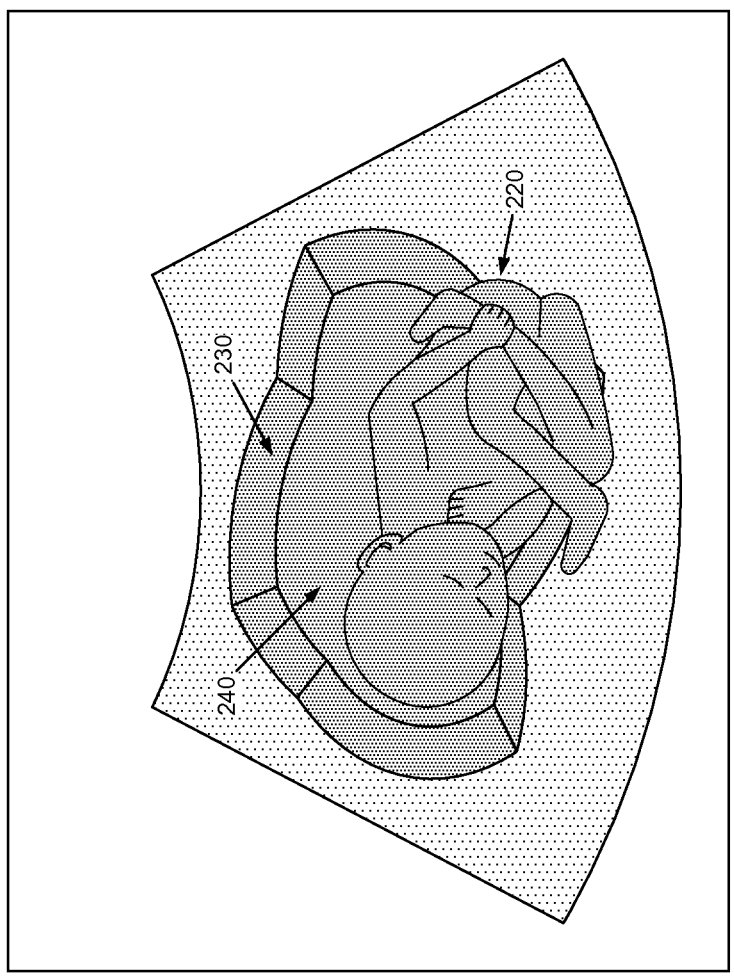
FIGS. 2A and 2B illustrate example use of amniotic fluid position detection based on shear wave propagation to optimize rendering of ultrasound images, in accordance with an embodiment of the invention.
Figure 2B:
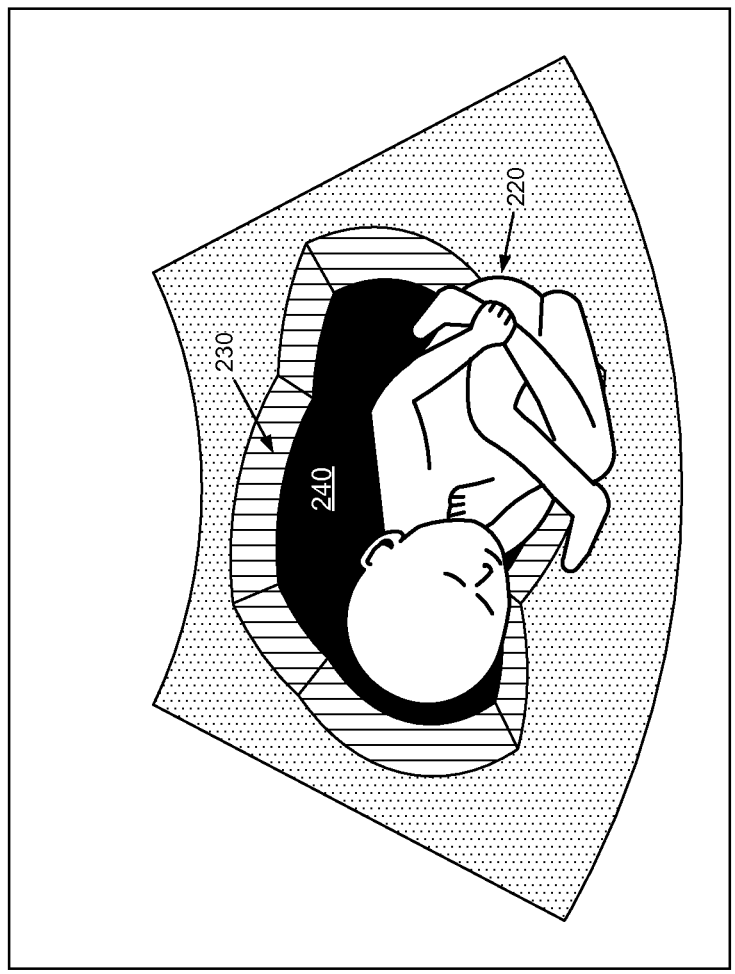

FIGS. 2A and 2B illustrate example use of amniotic fluid position detection based on shear wave propagation to optimize rendering of ultrasound images, in accordance with an embodiment of the invention. Shown in FIGS. 2A and 2B are ultrasound image frames 210 and 250, each of which comprising an ultrasound image. In particular, the ultrasound image frames 210 and 250 may correspond to use (or not) of shear wave propagation in an ultrasound system, such as the ultrasound system 100 of FIG. 1, to optimize rendering of ultrasound images during obstetric (OB) ultrasound examination.

Shown in the ultrasound image frame 210 is an ultrasound image that is rendered without enhancement based on shear wave propagation. The ultrasound image includes a fetus 220 surrounded by area 240 of amniotic fluid separating the fetus 220 from mother's tissue 230. Due to various causes, as described with respect to FIG. 1, the discrimination between the fetus 220 and the other objects—that is the mother's tissue 230 and the amniotic fluid area 240—may be insufficient, resulting in rendering of low (or unacceptable) quality.

Shown in the ultrasound image frame 250 is the ultrasound image of FIG. 2A, which is now rendered with enhancement based on shear wave propagation. In this regard, as result of the shear wave propagation, the amniotic fluid area 240 may be better identified (segmented), resulting in improved discrimination between the fetus 220 and the other objects. The better segmentation of the amniotic fluid area 240 and, as consequence, the better discrimination between the fetus 220 and other objects, may allow for enhanced rendering, particularly in manner where the visualization of the fetus 230 (and features thereof, such as facial features) is optimized in relation to the other areas.

Figure 3:
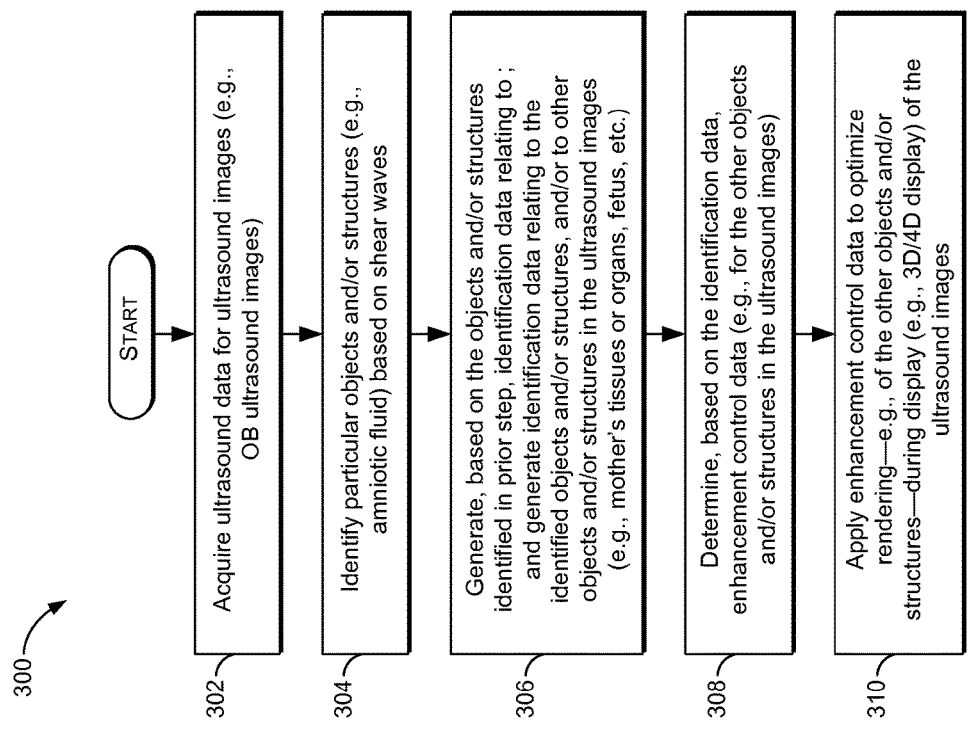
FIG. 3 is a flow chart illustrating example steps that may be performed for detecting amniotic fluid position based on shear wave propagation, in accordance with an embodiment of the invention.

FIG. 3 is a flow chart illustrating example steps that may be performed for detecting amniotic fluid position based on shear wave propagation, in accordance with an embodiment of the invention. Shown in FIG. 3 is a flow chart 300, which comprises a plurality of example steps, corresponding to an example method.

The technical effect of the method corresponding to flow chart 300 is providing adaptive visualization in volumetric ultrasound images by an ultrasound system (e.g., the ultrasound system 100). For example, the example steps of the method corresponding to flow chart 300 may be executed and/or performed by the various components of the ultrasound system 100.

It should be understood, however, that certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

In step 302, after a start step (in which an ultrasound system may be, for example, initialized and/or configured for ultrasound imaging), ultrasound data for ultrasound images (e.g., OB ultrasound images) may be acquired (e.g., using the ultrasound probe 104).

In step 304, particular objects and/or structures (e.g., amniotic fluid) may be identified based on shear waves. For example, shear wave propagation may be applied to the area corresponding to the ultrasound data acquired in the prior step, and the echo signals may be captured, and used (e.g., via the signal processor 140) in determining shear wave response characteristics (e.g., based on SNR) for different regions in the area.

In step 306, identification data relating to the particular objects and/or structures identified in prior step, as well as (possibly) to other objects and/or structures in the ultrasound images (e.g., mother's tissues or organs, fetus, etc.), may be generated. For example, identify the amniotic fluid area may allow for better identification of the fetus and/or mother's tissue. Thus, identification data relating to the amniotic fluid area and/or to the fetus may be generated once the amniotic fluid area is identified.

In step 308, enhancement control data may be generated, such as for the other objects and/or structures in the ultrasound images. For example, the signal processor 140 may determine various rendering adjustments for enhancing rendering (e.g., visualization) of the fetus area in the ultrasound images.

In step 310, the enhancement control data may be applied to optimize rendering of the other objects and/or structures during display (e.g., 3D/4D) of the ultrasound images.

As utilized herein the term "circuitry" refers to physical electronic components (e.g., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or." As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "example" means serving as a non-limiting example, instance, or illustration. As utilized herein, the terms "for example" and "e.g.," set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for optimizing detection of amniotic fluid based on shear wave propagation, and/or for use of that detection in enhancing rendering of ultrasound images.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method for ultrasound examination, comprising:
acquiring by an ultrasound device, ultrasound image data;
acquiring by the ultrasound device, shear wave related data for an area corresponding to the acquired ultrasound image data;
identifying by the ultrasound device, based on the shear wave related data, a particular structure within the area, wherein the identifying comprises determining presence and/or location of the identified structure within the area based on particular exhibited characteristics in response to shear wave propagation;
generating by the ultrasound device, based on the acquired ultrasound image data, one or more ultrasound images;
rendering by the ultrasound device, the one or more ultrasound images; and
controlling by the ultrasound device, based on the identified structure within the area, one or both of the generating and the rendering of the one or more ultrasound images, to adjust visualization of one or both of the identified structure and an adjacent structure, when the area is displayed.

2. The method of claim 1, wherein controlling the generating and/or the rendering of the one or more ultrasound images comprises adjusting B-mode brightness for one or both of the identified structure and the adjacent structure.

3. The method of claim 1, wherein the adjusting is configured to increase visualization of at least a portion of the identified structure or the adjacent structure.

4. The method of claim 1, wherein acquiring the shear wave related data comprises:
applying shear wave propagation to the area; and
assessing signal-to-noise ratio (SNR) for the applied shear wave propagation.

5. The method of claim 1, wherein the ultrasound examination comprises an obstetric (OB) ultrasound examination, and the area comprises one or more of: at least portion of a fetus, amniotic fluid surrounding the fetus, and tissue of a mother carrying the fetus, and comprising controlling one or both of the generating and the rendering of the one or more ultrasound images based on identifying at least one of the fetus, the amniotic fluid surrounding the fetus, and the tissue of the mother.

6. The method of claim 5, wherein the identified structure comprises the amniotic fluid surrounding the fetus.

7. The method of claim 5, comprising controlling one or both of the generating and the rendering of the one or more ultrasound images to enhance visualization of the at least portion of the fetus and/or discrimination between each of the at least portion of the fetus, the amniotic fluid, and the tissue of the mother.

8. The method of claim 1, wherein the identifying comprises one or both of:
- segmenting the area into separate structures based on the particular exhibited characteristics in response to shear wave propagation; and
- determining render-start points within the area based on the particular exhibited characteristics in response to shear wave propagation.

9. A system, comprising:
an ultrasound device for use in ultrasound examination, the ultrasound device comprising a processor, wherein:
the ultrasound device is operable to:
- acquire ultrasound image data;
- acquire shear wave related data for an area corresponding to the acquired ultrasound image data;
- generate based on the acquired ultrasound image data, one or more ultrasound images; and
- render the one or more ultrasound images; and the processor is operable to:
- identify based on the acquired shear wave related data, a particular structure within the area, wherein the identifying comprises determining presence and/or location of the identified structure within the area based on particular exhibited characteristics in response to shear wave propagation; and
- control based on the identified structure within the area, during an ultrasound examination, one or both of the generating and the rendering of the one or more ultrasound images, to adjust visualization of one or both of the identified structure and an adjacent structure, when the area is displayed.

10. The system of claim 9, wherein controlling the generating and/or the rendering of the one or more ultrasound images comprises adjusting B-mode brightness for one or both of the identified structure and the adjacent structure.

11. The system of claim 9, wherein the processor is operable to increase visualization of at least a portion of the identified structure or the adjacent structure.

12. The system of claim 9, wherein the ultrasound device is operable to apply shear wave propagation to the area; and the processor is operable to assess signal-to-noise ratio (SNR) for the applied shear wave propagation.

13. The system of claim 9, wherein the ultrasound examination comprises an obstetric (OB) ultrasound examination, and the area comprises one or more of: at least portion of a fetus, amniotic fluid surrounding the fetus, and tissue of a mother carrying the fetus, and wherein the processor is operable to control one or both of the generating and the rendering of the one or more ultrasound images based on identifying at least one of the fetus, the amniotic fluid surrounding the fetus, and the tissue of the mother.

14. The system of claim 13, wherein the identified structure comprises the amniotic fluid surrounding the fetus.

15. The system of claim 13, wherein the processor is operable to control one or both of the generating and the rendering of the one or more ultrasound images such that to enhance visualization of the at least portion of the fetus and/or discrimination between each of the at least portion of the fetus, the amniotic fluid, and the tissue of the mother.

16. The method of claim 9, wherein the processor is operable to:
- segment the area into separate structures based on the particular exhibited characteristics in response to shear wave propagation; and
- determine render-start points within the area based on the particular exhibited characteristics in response to shear wave propagation.

17. A non-transitory computer readable medium having stored thereon, a computer program having at least one code section, the at least one code section being executable by a machine for causing the machine to perform steps comprising:
- acquiring ultrasound image data;
- acquiring shear wave related data for an area corresponding to the acquired ultrasound image data;
- identifying by the ultrasound device, based on the shear wave related data, a particular structure within the area, wherein the identifying comprises determining presence and/or location of the identified structure within the area based on particular exhibited characteristics in response to shear wave propagation;
- generating by the ultrasound device, based on the acquired ultrasound image data, one or more ultrasound images;
- rendering by the ultrasound device, the one or more ultrasound images; and
- controlling during an ultrasound examination, based on the identified structure within the area, one or both of the generating and the rendering of the one or more ultrasound images, to adjust visualization of one or both of the identified structure and an adjacent structure, when the area is displayed.

18. The non-transitory computer readable medium of claim 17, wherein the controlling of one or both of the generating and the rendering of the one or more ultrasound images comprises adjusting B-mode brightness for one or both of the identified structure and the adjacent structure.

19. The non-transitory computer readable medium of claim 17, comprising acquiring shear wave related data based on signal-to-noise ratio (SNR) measurement for shear wave propagation applied to the area.

20. The non-transitory computer readable medium of claim 17, wherein the identifying comprises one or both of:
- segmenting the area into separate structures based on the particular exhibited characteristics in response to shear wave propagation; and
- determining render-start points within the area based on the particular exhibited characteristics in response to shear wave propagation.

* * * * *